United States Patent [19]

Pratt

[11] Patent Number: 4,525,307

[45] Date of Patent: Jun. 25, 1985

[54] MODIFIED ALUMINUM TRI-ALKOXIDE COMPOUNDS

[75] Inventor: Charles E. Pratt, Bethlehem, Pa.

[73] Assignee: Joseph Ayers, Inc., Bethlehem, Pa.

[21] Appl. No.: 519,560

[22] Filed: Aug. 2, 1983

[51] Int. Cl.$^3$ ............................................... C07F 5/06
[52] U.S. Cl. ..................................... 556/182; 106/20; 106/308 Q; 252/35
[58] Field of Search ................................ 260/448 AD

[56] References Cited

U.S. PATENT DOCUMENTS

| | | | |
|---|---|---|---|
| 2,687,423 | 8/1954 | Mesirow | 260/448 |
| 2,845,447 | 7/1958 | Carlson | 260/448 |
| 3,006,941 | 10/1961 | Mudrak et al. | 260/448 |
| 3,068,263 | 12/1962 | Smith | 260/448 |
| 3,305,571 | 12/1967 | Cenker | 260/448 |
| 3,651,131 | 3/1972 | Hay et al. | 260/448 AD |
| 3,905,936 | 9/1975 | Hawthorne | 427/216 |
| 3,920,713 | 11/1975 | Feichtinger et al. | 260/448 AD |
| 4,052,428 | 10/1977 | Lerner et al. | 260/448 AD |
| 4,132,724 | 1/1979 | Turner | 260/448 AD |

OTHER PUBLICATIONS

Chemical Abstracts 84 5990s, (1976).
Bradley et al., "Metal Alkoxides", Academic Press, New York, (1978), pp. 78–81.
Turner et al., J. Oil and Color Chemists Assn. 41, 769, (1958).

Primary Examiner—Helen M. S. Sneed
Attorney, Agent, or Firm—Curtis, Morris & Safford

[57] ABSTRACT

What are disclosed are aluminum isopropoxides modified for stability and improved flash point and useful in inks and as gellants for coatings, varnishes, paints and the like.

12 Claims, No Drawings

MODIFIED ALUMINUM TRI-ALKOXIDE COMPOUNDS

The present invention relates to modified aluminum isopropoxides having improved properties such as shelf life stability, improved flash point, etc. These compounds are especially useful in formulations requiring gelling and thickening properties such as in inks, coatings, varnishes, paints and the like. These properties provide for good heat setting and good "quick-set" in ink formulations demanded in a number of high speed printing processes such as in lithographic printing processes.

BACKGROUND OF THE INVENTION

It is well known that aluminum alkoxide structures are very complex. A summary of these structures, properties, etc., is found in Bradley et al., *Metal Alkoxides*, Academic Press, New York (1978), pages 78 to 81. Moreover, the use of these aluminum alkoxides in paints and coatings is also known, e.g. as discussed in the article published by Turner et al., *The Function of Aluminum Complexes as Structure Modifiers for Paint*, Journal of the Oil and Color Chemists Association, Vol. 41, November 1958, pages 769 et seq.

The production of aluminum alcoholates, i.e. aluminum alkoxides and liquid aluminum alkoxides and the like, has also been disclosed in a number of U.S. patents of which the following are known to the inventor: U.S. Pat. No. 2,687,423 issued Aug. 24, 1954 to Mesirow; U.S. Pat. No. 2,845,447 issued July 29, 1958 to Carlson et al.; U.S. Pat. No. 3,006,941 issued Oct. 31, 1961 to Mudrak et al.; U.S. Pat. No. 3,068,263 issued Dec. 11, 1962 to Smith; U.S. Pat. No. 3,305,571 issued Feb. 21, 1967 to Cenker; U.S. Pat. No. 3,920,713 issued Nov. 18, 1975 to Feichtinger et al.; U.S. Pat. No. 4,052,428 issued Oct. 4, 1977 to Lerner et al.; and U.S. Pat. No. 4,132,724 to Turner.

Aluminum alkoxides having the structural formula

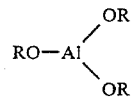

are referred to as aluminum tri-alkoxides and are desirable in cases where tri-functionally (i.e. three reactive sites) is desired. The monomeric structure

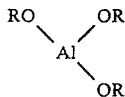

is used for ease of identification, although in actual occurrence there may be two, three, four or more of these aluminum tri-alkoxide molecules joined together by intermolecular forces to form corresponding dimeric, trimeric, tetrameric, or higher polymeric forms of the chemical. An example of the trimeric form of an aluminum tri-alkoxide as proposed in the above mentioned Bradley reference is:

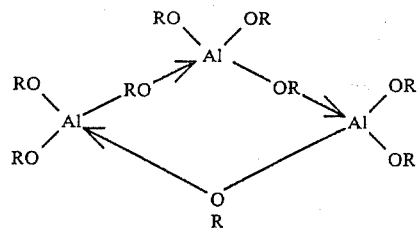

By the same reference, a proposed structure for the tetrameric form of an aluminum tri-alkoxide is:

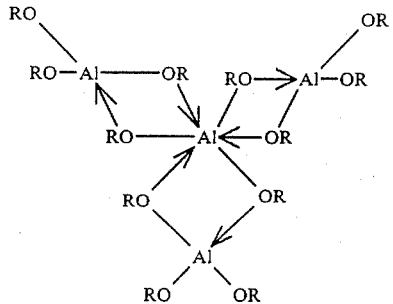

Whether the aluminum tri-alkoxide is in the monomeric, dimeric, trimeric, tetrameric, or higher polymeric form, it is always referred to as tri-functional because there are three reactive OR groups per atom of aluminum.

From the above literature and patent disclosures it is seen that one of the important considerations has been improved stability of the aluminum tri-alkoxides to hydrolysis and to solidification. This stability has been sought to be achieved by introducing acid groups or other reactive groups as replacements for one or more of the OR groups per atom of aluminum. In cases where stabilization is achieved by substituting an acid or other reactant group for one of the OR groups, it can be seen that the functionality of the aluminum compound is thereby reduced.

As discussed in the above mentioned literature references, these aluminum compounds react with moisture, hydroxyl groups, carboxylic acids, carboxyl groups present in other compounds, and carboxylic acid anhydrides. Hence, the usefulness of these compounds has been well established. However, an important commonly available aluminum tri-alkoxide, aluminum tri-isopropoxide, undergoes a physical change from a liquid to a solid during storage. This phenomenon has been described in the above mentioned literature and is explained herein. The polymeric structure of the aluminum isopropoxide is believed to be dimeric, trimeric, or a mixture of both when the product is first made. Upon ageing at ambient temperatures, it is generally believed to convert to the tetrameric form, which is a crystalline solid having rather poor solubility characteristics as compared to the freshly made compound in the liquid state.

Thus, aluminum tri-isopropoxide is only commercially available in the form of the solid tetramer, which is usually reduced to a finely divided powder prior to sale and use. Aluminum tri-alkoxides are highly reactive to atmospheric moisture, such reaction greatly reducing the activity of the product. The extremely high surface area of powdered aluminum tri-isopropoxide drastically increases the chance for moisture contact and thereby adversely affects the stability. Also, the solid tetrameric form has poor solubility in aliphatic solvents such as ink oils, and in many cases is only soluble at elevated temperatures.

On the other hand, aluminum tri-secondary butoxide remains liquid in storage at ambient temperatures and is often used in place of aluminum tri-isopropoxide where a tri-functional aluminum alkoxide is desired. However, aluminum tri-secondary butoxide also suffers from a number of serious shortcomings. One of these shortcomings is that the cost of secondary butyl alcohol is higher than that of isopropyl alcohol, making the cost of the aluminum tri-secondary butoxide generally higher than the cost of aluminum tri-isopropoxide. Another serious shortcoming of aluminum tri-secondary butoxide is that it typically has a flash-point lower than 100° F., which property requires it to be shipped and stored as a hazardous "red label" material. Many of the ink and other manufacturing plants desiring to use an aluminum tri-alkoxide are located in areas where the use and/or storage of "red label" materials is prohibited or in areas where insurance premiums would have to be drastically increased if "red label" materials were to be introduced. This "red label" condition of aluminum secondary butoxide can be eliminated by making a very dilute solution of the compound in ink oil solvents having a high boiling point prior to shipment from the plant in which the compound is manufactured. However, this practice increases manufacturing costs and presents an unreasonable increase in freight costs to the customer.

It is obvious that the industry would be greatly benefitted by the development of an aluminum tri-alkoxide that does not suffer from the shortcomings of the prior art. It is the object of this invention to disclose novel aluminum tri-alkoxide compounds which are composed mostly of isopropyl moieties and yet have improved properties with respect to resistance to solidification, increased solubility in hydrocarbon solvents, and also have improved flash point properties.

BRIEF DESCRIPTION OF THE INVENTION

It has now been found that if aluminum tri-isopropoxide is modified by substituting a higher alcohol for isopropyl alcohol in small molar amounts, the reactivity, the stability, and the flash point characteristics of the resulting compound are all improved.

The invention is thus predicated in part on the introduction of small molar amounts of an appropriate higher alcohol such that the aluminum content of these compositions is not appreciably reduced. The resulting solvent-free liquids (and even very slightly diluted solutions) are stable for a prolonged period. The outstanding activity of these compounds in inks, for heat set and "quick-set" applications, as well as for coatings, varnishes, paints and the like, makes them very desirable.

These improvements are achieved when the molar amounts of the introduced and reacted alcohol range from about 0.125 to about 0.5 moles per atom of aluminum. A preferred range is from about 0.175 to about 0.45 moles of the alcohol per atom of aluminum and a particularly preferred range is from about 0.25 to about 0.45 moles of alcohol per atom of aluminum.

As modifying alcohols, those having from $C_6$ to $C_{18}$ atoms are useful, with a preferred range being from $C_8$ to $C_{15}$, and a particularly preferred range being from $C_{10}$ to $C_{15}$. Tridecyl alcohol, i.e. $C_{13}H_{28}O$, is the most suitable alcohol. Tridecyl alcohol is commercially available as a mixture predominantly containing $C_{13}$ isomers, most being highly branched, with minor amounts of shorter and longer chain alcohols.

This introduction of appropriate alcohols provides a liquid product having improved solubility characteristics in the hydrocarbon solvents which are compatible with the above recited ink, paint, varnish and like compositions and formulations.

Solvents suitable for use with this invention include the petroleum-derived high-boiling (350°–650° F.) aliphatic hydrocarbon ink oil solvents commercially available under the trademarks "WITSOL" 45 and 50 manufactured by Witco Chemical Co.; the "MAGIE" 400, 470, 520, 620 oils, "MAGIESOL" 40, 44, 47, 52 and 62 manufactured by Magie Bros. Oil Co., as well as lower boiling aliphatic and aromatic hydrocarbon solvents used in paint, varnishes, adhesives, and like formulations. The above list of solvents is for illustration only and is not intended exhaustive. Other solvents suitable for use in this invention are the lubricating oil base stocks, both paraffinic and naphthenic, having viscosities at 100° F. ranging from about 35 to 50,000 Saybolt Universal Seconds (SUS).

"WITSOL 45", typical of the ink oil solvents, having a boiling range of about 450° F. to 543° F., has been used herein to study the solubility of these novel compounds and it has been discovered that high solids solutions of these compounds in this solvent have flash points higher than 100° F. This surprising result now makes it possible for industrial consumers to use a liquid tri-alkoxide with a relatively high aluminum content without the attendant danger associated with low flash point prior art compounds.

Storage stability of some of these novel compounds is such that no "red label" precautions are required, thus making available the use of these novel aluminum alkoxides in many heretofore prohibited areas.

As discussed earlier, the low flash point of the prior art compounds and the need to dilute them excessively makes their transportation costs prohibitive. A benefit associated with the present compounds is that the present compounds can be shipped without the excessive dilution required with the prior art compounds.

In addition, the present compounds, being liquid, are easily and readily diluted to give the desired aluminum content in final compositions. For example, for shipping, the compounds are diluted to give solutions containing 50 to 95 percent by weight of the compounds, preferably from 50 to 80 percent by weight.

Typically, in ink or varnish formulations these compounds are used in an amount from 0.5% to 5%, but usually the amount is between 1% and 5% by weight of the ink vehicle.

In accordance with the present invention, the compounds are prepared as given in the Examples below. These Examples are for the purpose of comparison and/or illustration and are not intended to limit the broader scope of the invention.

Still further, these examples are for purposes of illustrating not only the prior art failings, but also to distinguish the present invention from the prior art and show the nonobvious properties or novel properties heretofore not recognized.

EXAMPLE 1

7.0 grams of tridecyl alcohol (available from Exxon Chemical Corp.) were added to 20.4 grams of aluminum tri-isopropoxide. The amount added is 0.35 mole per atom of aluminum. The temperature of the mixture was raised to a point where isopropyl alcohol starts distilling off. Heating was continued until the temperature of the mass reached 150° C. and then was held at that temperature for 2 hours. The reaction is an alcohol exchange reaction. The resulting product (an approximate 0.35 mole addition product) is a permanent liquid. This liquid is soluble in ink oil solvents in all proportions. "WITSOL 45", as a typical ink solvent, is used for dilution.

EXAMPLE 2

635.7 grams of aluminum tri-isopropoxide were placed in a 3-necked 2000 ml flask equipped with a stirrer and a heating mantle. The heat was turned on to melt the compound, at which time 109.2 grams of tridecyl alcohol (0.175 mole/atom of Al) were added to the flask. Heating was continued while isopropyl alcohol distills off. The temperature was slowly raised to 150° C. and held between 150° C. and 160° C. for a period of two hours. On cooling, the clear liquid product eventually crystallized to form a heterogeneous mixture of crystals and liquid.

While the above compound was still in a liquid state (prior to crystallization), a portion weighing 271.0 grams was taken from it. 36.5 grams of "WITSOL 45" were added to this portion and the resultant high solids ink oil solution was heated to 200° C. and held at that temperature for 15 minutes. This ink oil solution was then cooled and held for analysis and observation. It was found to contain 9.6% aluminum, was homogeneous and clear, and had improved stability in solvated form, i.e. the solution was still stable after six months.

EXAMPLE 3

3.5 grams tridecyl alcohol were added to 20.4 grams aluminum tri-isopropoxide (0.175 mole per atom of aluminum) and 4.0 grams "WITSOL 45". This mixture was heated and stirred while isopropyl alcohol boiled off. Heating was continued to a temperature of 150° C. and the mass is held at that temperature for a period of two hours. The result was a clear liquid 85.1% dissolved solids solution of the modified aluminum tri-isopropoxide in ink oil solvent. The solution was still stable after six months showing improved solubility of the novel compound.

EXAMPLE 4

418.1 grams of aluminum tri-isopropoxide were added to a 3-necked flask equipped with a stirring motor and a heating mantle. Heat was applied to melt the compound, at which time 145.4 grams of tridecyl alcohol (0.35 mole per atom of aluminum) and 115.5 grams of "WITSOL 45" were added. Heating was continued while isopropyl alcohol boiled off and the temperature slowly rose to 300° F. The temperature is held between 300° F. and 310° F. for 20 minutes and the mixture was then allowed to cool. The resultant product was a permanently liquid high solids solution of the 0.35 molar substituted aluminum composition of this invention. The product was analyzed and found to have an aluminum content of 8.53% and a flash point of 160° F.

8.53% aluminum corresponds with the aluminum content of a 77.8% solids solution of aluminum tri-secondary butoxide. However, aluminum tri-secondary butoxide has a low flash point and requires an ink oil dilution to less than 40% solids content (60% by weight solvent addition) to have a flash point of 100° F. or higher. For comparison it is convenient to reduce both the compound of this invention and aluminum tri-secondary butoxide to an approximately equal aluminum content basis with the same ink oil solvent. The data so obtained are placed for comparison in following Table I:

TABLE I

| Product | Aluminum Assay | Flash Point* |
| --- | --- | --- |
| Compound of Example 4 | 8.53% | 160° F. |
| Aluminum tri-secondary butoxide | 8.57% | 85° F. |
| Compound of Example 4 | 3.64% | 190° F. |
| Aluminum tri-secondary butoxide | 3.70% | 90° F. |

*All flash points are determined according to the method of ASTM-D92, modified to break the surface skin mechanically before each pass of the flame.

EXAMPLE 5

Corresponding substituted compounds were obtained following the procedure as in Example 1 above using decyl alcohol, nonyl alcohol, iso-octyl alcohol, and 2-ethyl-hexanol, adjusting for about equal aluminum content with "WITSOL 45", i.e. about 8.8% Al, and using the alcohol in an amount of 0.35 mole/gram atom of Al, based on the starting isopropoxide compound. All of the above compounds were still clear liquid solutions after five months, indicating improved solubility characteristics over unmodified aluminum tri-isopropoxide. For comparison, unmodified aluminum tri-isopropoxide was diluted to the approximately same aluminum content with the same ink oil solvent, "WITSOL 45", and treated with the same heating profile as the above samples. The unmodified aluminum tri-isopropoxide solution crystallized within one day. For comparative purposes these data are shown below in following Table II:

TABLE II

| Modifying Alcohol | Al Assay (%) | Dissolved Solids (%) | Results |
| --- | --- | --- | --- |
| decyl alcohol | 8.60 | 79.8 | Still clear after 5 months |
| nonyl alcohol | 8.80 | 76.2 | Still clear after 5 months |
| iso-octyl alcohol | 8.85 | 74.6 | Still clear after 5 months |
| 2-ethyl hexanol | 8.88 | 74.5 | Still clear after 5 months |
| unmodified aluminum tri-isopropoxide | 8.80 | 66.6 | Crystalline solid - 1 day |

EXAMPLE 6

Using the same procedure as Example 2, 451.4 grams of aluminum tri-isopropoxide were modified with 110.7 grams of tridecyl alcohol (0.25 mole of alcohol per atom of aluminum). 44.2 grams of "CORAY 22" oil, which is a naphthenic lubricating oil stock having an approximate viscosity at 100° F. of 100 Saybolt Universal Seconds and is a product of Exxon Corp were added to this compound. The resultant mixture was analyzed and found to contain 10.3% of aluminum and was a lubricating oil solution of a compound of this invention suitable for the manufacture of aluminum complex grease. The product was still a clear solution after 5 months, indicating improved solubility characteristics in lubricating oil stock.

In other, like, applications, the novel compounds show improved characteristics.

While the starting compounds have been illustrated as having a particular polymeric structure, this illustration has been only in aid of understanding the invention. The exact polymeric structures of these compounds are still being questioned; hence, the inventor does not wish to be bound by any theory. However, for the claimed compounds and compositions, the improved characteristics have been established.

What is claimed is:

1. A modified aluminum tri-isopropoxide compound wherein about 0.125 to about 0.50 mole of isopropoxide, per atom of aluminum, is replaced with a $C_6$- to $C_{18}$- alkoxide.

2. The compound as in claim 1 wherein the replacing alkoxide is a $C_8$- to $C_{15}$- alkoxide.

3. The compound as in claim 1 wherein the replacing alkoxide is a $C_{10}$- to $C_{15}$- alkoxide.

4. The compound as in claim 1 wherein the $C_6$- to $C_{18}$- alkoxide is tridecyl alkoxide.

5. The compound as in claim 1 wherein the $C_6$- to $C_{18}$- alkoxide is present in an amount from 0.175 to 0.45 mole per atom of aluminum.

6. The compound as in claim 1 wherein the $C_6$- to $C_{18}$- alkoxide is present in an amount from 0.25 to 0.45 mole per atom of aluminum.

7. The compound as in claim 6 where the $C_6$- to $C_{18}$- moiety is tridecyl alkoxide.

8. A solution containing from 50 to 95 percent by weight of a compound as in claim 1 dissolved in a hydrocarbon solvent.

9. A solution as in claim 8 containing from 50 to 80 percent by weight of said compound.

10. A solution as in claim 8 wherein said solvent is an aliphatic hydrocarbon solvent.

11. A solution as in claim 8 wherein said solvent is a petroleum derived naphthenic or paraffinic hydrocarbon having a viscosity from about 35 to about 50,000 SUS at 100° F.

12. A solution as in claim 8 wherein said solvent is a petroleum derived aliphatic hydrocarbon having a boiling range in the range from about 350° F. to about 650° F.

* * * * *